United States Patent
Hildebrand et al.

(10) Patent No.: US 7,087,078 B2
(45) Date of Patent: Aug. 8, 2006

(54) TUBULAR VASCULAR IMPLANTS (STENTS) AND METHODS FOR PRODUCING THE SAME

(75) Inventors: Gesine Hildebrand, Berlin (DE); Johannes Tack, Berlin (DE); Helmut Kaeufer, Mettmann (DE); Hans-Martin Wache, Berlin (DE); Thomas Mueller, Berlin (DE); Peter Ewert, Berlin (DE)

(73) Assignee: Schering AG, Berlin (DE)

( * ) Notice: Subject to any disclaimer, the term of this patent is extended or adjusted under 35 U.S.C. 154(b) by 251 days.

(21) Appl. No.: 10/432,156

(22) PCT Filed: Nov. 21, 2001

(86) PCT No.: PCT/DE01/04424

§ 371 (c)(1),
(2), (4) Date: Nov. 24, 2003

(87) PCT Pub. No.: WO02/41929

PCT Pub. Date: May 30, 2002

(65) Prior Publication Data

US 2004/0093074 A1 May 13, 2004

Related U.S. Application Data

(60) Provisional application No. 60/252,891, filed on Nov. 27, 2000.

(30) Foreign Application Priority Data

Nov. 21, 2000 (DE) .......................... 100 57 817

(51) Int. Cl.
*A61F 2/06* (2006.01)

(52) U.S. Cl. ....................... 623/1.18; 623/1.2
(58) Field of Classification Search ................ 623/1.15, 623/1.22; 427/2.24, 456

See application file for complete search history.

(56) References Cited

U.S. PATENT DOCUMENTS

| 5,040,548 A | | 8/1991 | Yock |
| 5,061,273 A | | 10/1991 | Yock |
| 5,350,395 A | | 9/1994 | Yock |
| 5,451,233 A | | 9/1995 | Yock |
| 5,968,091 A | * | 10/1999 | Pinchuk et al. ............. 623/1.16 |
| 6,036,715 A | | 3/2000 | Yock |
| 6,150,489 A | | 11/2000 | Pudleiner et al. |
| 6,153,252 A | * | 11/2000 | Hossainy et al. ............ 427/2.3 |
| 6,165,197 A | | 12/2000 | Yock |
| 6,210,432 B1 | | 4/2001 | Solem et al. |
| 6,716,957 B1 | | 4/2004 | Tunc |
| 2001/0018611 A1 | | 8/2001 | Solem et al. |

FOREIGN PATENT DOCUMENTS

| DE | 19638570 | 3/1998 |
| DE | 19755872 | 6/1999 |
| EP | 0970711 | 1/2000 |
| WO | WO 9526762 | 10/1995 |
| WO | WO 02/060352 A1 | 8/2002 |

OTHER PUBLICATIONS

Robert O. Bonow, et al., "Guidelines for the Management of Patients with Valvular Heath Disease, " Report of American College of Cardiology/American Heart Assoc. Task Force on Practice Guidelines (Committee on Management of Patients with Valvular Heart Disease), American College of Cardiology and American Heart Assoc., Inc., 1998, pp. 1949–1984.

* cited by examiner

*Primary Examiner*—Corrine McDermott
*Assistant Examiner*—Hieu Phan
(74) *Attorney, Agent, or Firm*—Millen, White, Zelano & Branigan, P.C.

(57) ABSTRACT

New tubular vascular implants (stents) that consist of biocompatible, thermoplastic material that have a shape memory and that contain at least one active ingredient are described. In addition, a process for their production and their use as vascular implants for prophylaxis of restenosis are described.

18 Claims, 3 Drawing Sheets

TUBULAR VASCULAR IMPLANTS (STENTS) AND METHODS FOR PRODUCING THE SAME

RELATED APPLICATION

Figure 1:
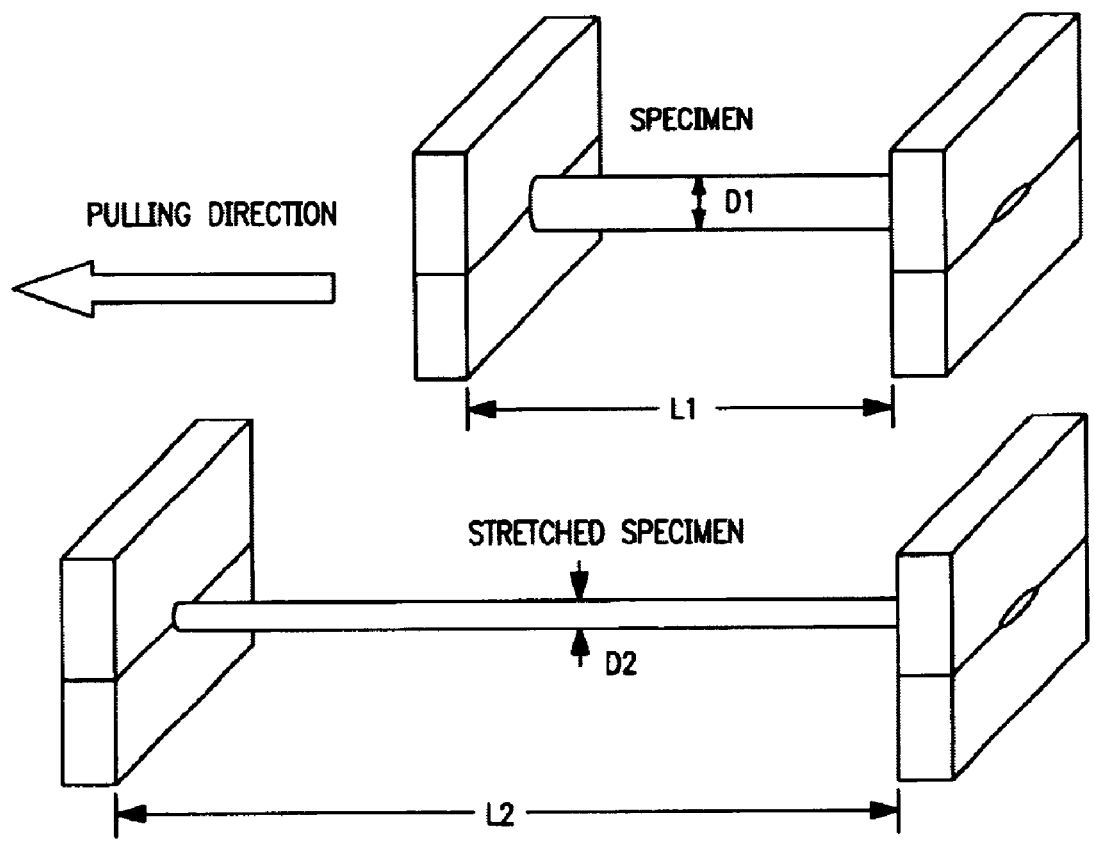

This present application claims priority 371 of PCT/DE01/04424, filed Nov. 21, 2001 which claims benefit of U.S. Provisional Application 60/252,891, filed Nov. 27, 2000.

The invention relates to the subject that is characterized in the claims, i.e., new tubular vascular implants (stents) as well as a process for their production.

Cardiovascular diseases are common diseases in industrial nations. They represent one of the most frequent causes of death. In most cases, cardiovascular diseases are caused by arteriosclerosis. This is an inflammatory, fibroproliferative disease that is responsible for 50% of all deaths in the USA, Europe and Japan (Ross 1993, Nature 362: 801–809). With its peripheral manifestation, it threatens the upkeep of the extremities; with its coronary manifestation, the risk of fatal myocardial infarction exists and with a supraortal attack creates the danger of stroke.

Treatment of arteriosclerosis is currently carried out in various ways. In addition to conservative measures (e.g., the lowering of the cholesterol level in the blood) and the bypass operation, mechanical dilatation (angioplasty) as well as intravascular removal of atheromatous tissue (atherectomy) of stenotic segments in peripheral arteries and coronaries has been established as an alternative in regular clinical practice.

As stated below, the above-mentioned methods, however, are associated with a considerable number of drawbacks.

The value of mechanical rechanneling processes is greatly diminished by vascular occlusions as a result of vascular tears and dissections as well as acute thromboses (Sigwart et al. 1987, N. Engl. J. Med. 316: 701–706). The long-term success is jeopardized by the reoccurrence of constrictions (restenoses). The CAVEAT study on 1012 patients thus indicated that the restenosis rate six months after intervention was 50% in the coronary atherectomy and even 57% in the coronary angioplasty (Topol et al. 1993, N. Engl. J. Med. 329: 221–227). In addition, sudden vascular occlusions occurred in this study in 7% of the atherectomy patients and in 3% of the angioplasty patients. Nicolini and Pepine (1992, Endovascular Surgery 72: 919–940) report on a restenosis rate of between 35 and 40% and an acute occlusion rate of 4% after angioplastic intervention.

To counteract these complications, different techniques were developed. This includes the implantation of metallic endoprostheses (stents), (Sigwart et al. 1987, N. Engl. J. Med. 316: 701–706; Strecker et al., 1990, Radiology 175: 97–102). The stent implantation in large-caliber arteries, e.g., in occlusions in the pelvis, has already become a therapy modality to be used primarily. The use of stents in the femoral arteries has already shown disappointing results with a primary openness rate of 49% and a reocclusion frequency of 43% (Sapoval et al., 1992, Radiology 184: 833–839). Also unsatisfactory results mainly caused by restenosis were achieved with currently available stents in the coronary arteries (Kavas et al. 1992, J. Am. Coll. Cardiol 20: 467–474).

As causes for the restenoses that frequently occur after mechanical interventions, it is assumed that the interventions induce a proliferation and migration of smooth muscle cells in the vascular wall. These result in a neointimal hyperplasia and the observed restenoses in the treated vascular sections (Cascells 1992, Circulation 86: 723–729, Hanke et al. 1990, Circ. Res. 67: 651–659, Ross 1993, Nature 362: 801–809).

In European Patent EP 706 376, metal wire endoprostheses are described that are coated with a polymer that contains taxol as an active ingredient and releases this active ingredient little by little into the surrounding tissue. Taxol has an anti-angiogenic action, and it is asserted that the thus coated stents would be suitable for preventing restenosis. No results of clinical studies to support this hypothesis are disclosed, however.

In German Patent DE 198 12 160 C1, molded elements that consist of active ingredient-containing thermoplastic polyurethanes are described, which contain antibiotically active substances in a homogeneous distribution. The molded elements that are described are in particular central venous catheters.

In U.S. Pat. No. 5,962,004, implants are described that consist of a polyurethane-based material with a glass transition temperature of between 20° C. and 60° C. The implants have a shape memory.

In U.S. Pat. No. 5,716,410, a temporary stent and its use are described. The stent consists of polyurethane and has a shape memory. The polyurethane has a glass transition temperature of between 40° C. and 80° C., whereby a glass transition temperature of 45° C. is preferred.

In International Patent Application WO 99/42528, polymers are described that have a shape memory. The transition temperature is between −30° C. and 270° C. Preferred polymers are polyurethanes, and the latter can be used to produce, e.g., stents.

In U.S. Pat. No. 5,458,935, thermoplastic polyurethanes are described that have a hardness of between 60 and 70 Shore D. The polymers are used to produce hoses.

In German Laid-Open Specification DE 197 55 872 A1, plastic parts with shape memory that consist of thermoplastic material that are suitable as vascular implants are already described. The implants that are described there can be made from any thermoplastic material.

All previous pharmacological and mechanical interventions in patients have not been able to prevent restenosis up until now (Muller et al. 1992, J. Am. Coll. Cardiol. 19: 418–432). There is therefore also a need for suitable means that are suitable for the prophylaxis of restenosis.

The object of this invention is to develop especially suitable tubular vascular implants that contain at least one active ingredient that is optionally released at high concentration and over an extended period to the surrounding tissue.

This object is dissolved by those tubular vascular implants that comprise a thermoplastic polyurethane with a Shore hardness of 73A to 80D, have a shape memory and a shape-recovery temperature of between 35° C. and 50° C., and contain at least one active ingredient.

The combination of the previously mentioned features that achieve the above-mentioned object is preferred.

It was found, surprisingly enough, that aliphatic, polycarbonate-based thermoplastic polyurethanes are especially well suited for the production of vascular implants with shape memory for the prophylaxis of restenosis. Especially suitable are so-called carbothanes of the Thermedics, Inc. Company, which are available in a broad range of degrees of hardness, colors and x-ray contrast medium additions. All of these plastics are suitable for use as medicinally pure biomaterials and have passed the U.S.P.

Class V1-test, the MEM elution test and other relevant tests to indicate their biocompatibility and biostability. The carbothanes have an extraordinarily high hydrolytic and oxidation stability, which indicate excellent long-term biostability.

It has also been found, surprisingly enough, that material types with a high degree of hardness are especially well suited for the above-mentioned purpose. Suitable polyurethanes from the class of carbothanes have a Shore hardness of between 73A and 80D.

In the examples below, tests with polyurethanes of various degrees of hardness are described in detail, whereby it was discovered that the polymer PC-3572D with the mechanical properties described in Table 1 is best suited for the production of vascular implants for prophylaxis of restenosis.

In addition, the plastic parts according to the invention can also be produced in principle by immersion or pouring, since the polyurethanes that are used are soluble in a number of solvents. As solvents, for example, chloroform, cyclohexane, cyclohexanone, cyclopentanone, dimethyl acetamide, dimethylformamide, dimethyl sulfoxide, dioxane, methylene chloride, N-methyl-pyrrolidone, tetrahydrofuran, acetonitrile, acetone, diethyl ether, ethanol, ethyl acetate, hexane, isopropyl alcohol, methanol, methyl-ethyl-ketone, toluene, trichloroethane, hydrochloric acid, sodium hydroxide solution or common salt solution are suitable. The immersion and pouring is somewhat more expensive in comparison to the above-described extrusion and injection-molding process, but it has the advantage that no high temperatures are necessary in contrast to the above-mentioned process. This type of production can be the sole

TABLE 1

Mechanical Properties of Carbothane PC-3572D

| Product | Tearing stress [N/mm$^2$] | Elongation at rupture [%] | Tensile modulus [N/mm$^2$] | Flexural modulus [N/mm$^2$] | MFI 8 [g/10 min] | Hardness testing [Shore] |
|---|---|---|---|---|---|---|
| PC-3572D | 57.8 | 360 | 22.712 | 625.6 | 4.8 at 210° C. | 71 D (hard) |

The production of vascular implants basically follows the processes that are described in German Laid-Open Specification DE 197 55 872 A1. It is already explained there that plastic parts can be produced basically with the aid of two processes: on the one hand with the aid of the injection-molding process, and on the other hand by extrusion.

In the injection-molding process, the plastic granulate or powder is filled into the sink hopper of the injection-molding machine, which feeds into a horizontal hollow cylinder, where it is then conveyed on by the turning of a screw that is operated in most cases by an electric motor. The hollow cylinder is heated so that a plastification is carried out as a result of heating via a turbulence and the shearing action of the plastic. The plasticized plastic is collected ahead of the end of the screw. By a piston-like forward motion of the screw that is produced by oil hydraulics in most cases, it is then injected in a short time with high force into the closed form of the tool. While the shaped part cools off in the mostly water-cooled tool, the screw, with simultaneous plasticization, conveys the plastic for the next injection-molded part into the storage space ahead of the tip of the screw.

The injection-molding process is expensive for tubular parts in the tool device, since the hollow space is produced by a core and the latter is difficult to remove after the shrinkage by the cooling of the material. The design of the process is expensive, but a very exact and reliable manufacturing is possible in the injection-molding process. The processing temperature of the carbothane melt is 160 to 240° C., preferably 180 to 200° C., in this process.

An extruder has a plasticizing unit that is similar to an injection-molding machine. The latter does not operate with its screw in the cylinder into a storage space, but rather directly into the nozzle-like tool, in which the forming takes place. For the production of any type of endless profiles, tubes and hoses, extrusion is an especially well suited means, since even larger amounts can be processed extremely economically and reproducibly. The processing temperatures of carbothanes are approximately 200 to 260° C. here, preferably 220° C.

possible processing option in the case of a planned addition of thermolabile medicinal active ingredients.

In the production by immersion, the thermoplastic material is converted into a physical solution with the aid of a suitable solvent. Then, a thin plastic layer is applied on the core by short-term immersion of a core element. The wall thickness of the thus formed plastic element is determined by the number of repetitions of this process. In addition, wall thickness and quality of the plastic element can be influenced by the concentration of the plastic in the solvent.

The vascular implants contain at least one active ingredient, whereby active ingredient is defined as both medicinal active ingredients, which are released to the surrounding tissue, and x-ray-opaque materials (x-ray contrast media), such as, e.g., barium sulfate, zirconium oxide or iodine-containing compounds. For example, the active ingredients can be added directly to the monomer during polymerization and then can be dispersed homogeneously in the plastic powder or granulate or added during the processing of the polyurethane melt or solution into the vascular implant in the desired amount. The active ingredients are preferably dissolved or dispersed in the polymer, whereby the active ingredient can be dissolved both in the melt and in the organic solution of the polymer. The active ingredient admixture of up to 30% by weight of active ingredient in the polyurethane thus can be achieved. The processing is carried out as described above by extrusion, injection-molding, immersion or pouring, whereby in the extrusion or injection-molding process, only thermally stable active ingredients can be used. Primarily active ingredients that have an antiproliferative action on the endothelium and/or smooth muscle cells or those that prevent an overflowing neointima from starting to form by keeping the thrombus from attaching to the vascular wall are suitable. In their mode of operation, these active ingredients can work in quite different ways and can be known by quite different applications (e.g., cardiology, oncology).

If both the active ingredient and the polymer in the same solvent are soluble, a solution can be produced that contains both substances. The active ingredient content is freely adjustable up to a proportion of 30% by weight relative to the polymer. If solutions of different active ingredient concentrations are used, a molded element can be produced based on the desired release profile that has different active ingredient concentrations or else different active ingredients in each of its various layers.

Examples of suitable active ingredient groups are, i.a., active ingredients that control the cell proliferation (e.g., cytostatic agents, antiangiogenic active substances), active ingredients that prevent inflammation at the site of application (e.g., corticoids, NSAID), or active ingredients that inhibit the formation of thrombi (e.g., heparin, hirudin), or angiogenesis growth factors. Especially suitable are the active ingredients angiostatin, endostatin, iloprost, prostacyclin, endoxan, methotrexate, heparin, hirudin, clopidogrel, paclitaxel, doxazosin, thalidomide, rapamycin, trapidil, acetylsalicylic acid, dexamethasone, prednisolone, triamcinolone acetonide as well as epothilone.

As an alternative, these active ingredients can be applied exclusively to the inside and/or outside surface of the vascular implants or can be introduced during the immersion process at various concentrations in individual layers to model the release profile of the active ingredient. In this way, vascular implants are produced in which the active ingredient concentration varies over the cross-section of the implant. It is also possible to attach the plastic to the surface with an active ingredient as a semifinished product or as a finished stretched stent or to press the active ingredient into the plasticized surface area. The latter can also be carried out by rolling or pressing. It is also possible to process different active ingredients in a stent, so that, e.g., one active ingredient is released to the vascular wall and another active ingredient is released to the vascular lumen.

It thus is possible to produce vascular implants that have medicinal active ingredients on their inside and/or outside surface, in a specific surface area or in the entire area.

In especially advantageous cases, the active ingredients have a positive influence on the hardness, structure and strength of the host polymer. The addition of polycarbonate can be reduced by this synergy effect.

The addition of x-ray contrast media as active ingredients is then necessary if the thermoplastic polyurethane in the x-ray image is to be distinguished from the surrounding tissue. As x-ray contrast media, strongly absorbent substances, such as, e.g., barium sulfate, zirconium oxide or iodine-containing compounds, are suitable. If contrast medium is worked into the polymer, the contrast medium is not dissolved but rather only dispersed, such that there is a homogeneous dispersion in the plastic. Since the contrast medium does not go into solution, it remains after the introduction into the organism in the polymer matrix, is not removed from the polymer and therefore also is not released like the other medicinal active ingredients. The contrast medium concentration in the plastic therefore remains constant.

Shape memory is then imposed by stretching and setting on a plastic part that is produced by injection-molding, extrusion, immersion or pouring as already described in DE 197 55 872 A1. This production step can be referred to as the actual stent production, in which the actual product is produced in its finished application diameter from a blank.

During the process according to the invention, the stretching process is a drawing of a specimen in length. In this respect, the blank is set on a specimen with a defined length in a clamping device. This clamping device prevents a later slipping of the sample by specific pressure on the sample ends.

The pressure (and thus the clamping force) can be exerted on the sample, for example, by means of a pneumatic cylinder. In each case, the sample ends are clamped. The specimen that is used has, for example, an initial length of 70 mm with an outside diameter of about 4 mm. Each end is clamped, e.g., on a length of 10 mm, so that in stretching, an initial sample length between the clamping points of about 50 mm exists.

To make possible a defined temperature profile, the sample is found during the stretching process in a tempered fluid, preferably in a tempered liquid such as, e.g., water. FIG. 1 diagrammatically shows a specimen in its initial dimensions, which is stretched in a tempered fluid in the stretching device.

Via a stepper motor and a threaded rod, the distances between the clamping points can be varied. If the clamping points are moved away from one another, the stretched sample is drawn longitudinally. Attention must be paid that the holding force, which exerts the sample clamping on the sample ends, is greater than the tensile force, and that the sample resists the pulling, since otherwise the sample would slip out from the clamping point.

As diagrammatically shown in FIG. 1, the specimen can be stretched (drawn) from an initial length L1 between the clamping points (e.g., L1=50 mm) to an end length L2 between the clamping points (e.g., L2=150 mm) and in this case undergoes a narrowing of diameter of D1 (e.g., D1=4 mm) to D2 (e.g., D2=2.5 mm).

The motor speed can be set variably, in this case a speed of 20 rpm was selected. With this screw pitch of the spindle of 2.5 mm, this corresponds to a stretching speed of 50 mm/min.

In the lower part of FIG. 1, the specimen is shown diagrammatically within the tempered fluid in the stretched state.

After the stretching process, the specimen takes up its internal stresses as much as possible through the relaxation of the plastic. During the setting phase that is now occurring, the temperature must be kept absolutely constant, since this temperature corresponds to the later activation temperature. After the setting phase, the liquid that is used for tempering is drained off and replaced by cooled liquid. As a result, a quick cooling is achieved. The cooling temperature is maintained until the specimen is thoroughly cooled.

To examine shape recovery, the specimen is slowly heated at a heating rate of 1° C./min. Starting from a specific temperature, shape recovery of the sample begins. With the help of a measured-value recording system, the temperature and the path covered can be recorded continuously. In this case, within a specific temperature range, maximum shape recovery can be expected. Shape recovery ends when the sample has again reached its initial length of, for example, 70 mm. An embodiment with detailed parameters is described in the examples below.

The shape recovery maximum can be set so that it is between 35° C. and 50° C., for example 37° C. This temperature is independent of the glass transition temperature of the polymer. It is determined exclusively from the parameters used during stretching and is freely adjustable within wide ranges. In the described process, the temperature range of the shape-recovery maximum is an exclusive process control value and not a value that can be influenced by material control.

The stretched stent can then be brought to the site of application with a catheter. A prior flushing of the catheter with common salt solution tempered to, for example, 10° C., can ensure a temperature at the tip of the catheter of 31° C. or less for a period of 2 minutes after the flushing. Thus, during the actual stent application, a defined temperature jump can be achieved that simplifies the application. If the stent is applied in this way, it can be brought to its target site in dimensionally stable form and begins there, triggered by the body temperature, with the shape recovery in its initial form and thus with the widening in diameter. The widening in diameter takes place in a period of a few minutes. The stent was then pressed tightly to the vascular wall and can no longer slip.

The tubular vascular implants according to the invention are especially well suited for the prophylaxis of restenosis but can also—depending on the addition of active ingredient—be implanted as bile duct stents or in other regions of the body. The incorporated pharmaceutical substances are released into the blood or into the surrounding tissue depending on their solubility and their dispersion coefficient. Additives that are used only to determine the position by means of x-rays, e.g., the water-insoluble barium sulfate, are not released. The position of the stent even after implantation can thus always be determined again.

The examples below illustrate the invention without intending that it be limited to these examples.

EXAMPLE 1

Figure 2:
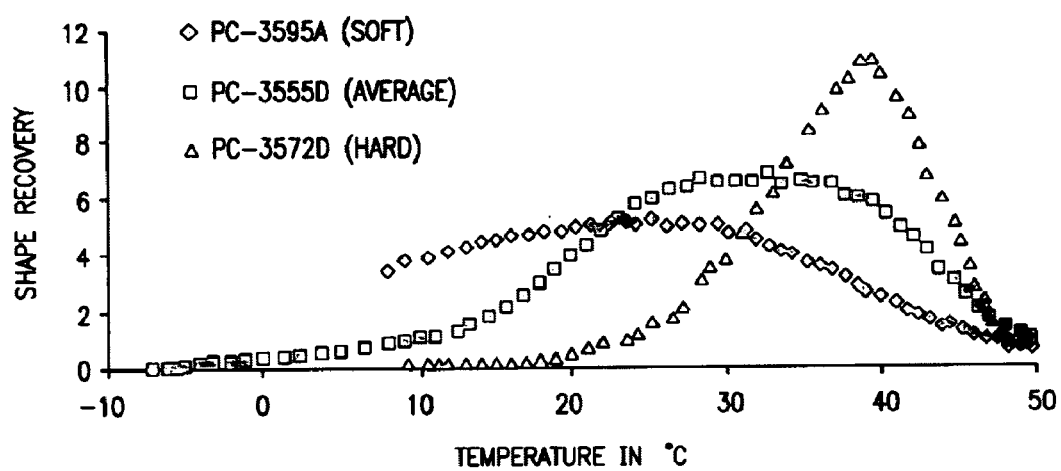

Comparison of Plastic Parts, Which were Produced from Polyurethanes of Various Degrees of Hardness Tests for sample elasticity were performed with carbothanes PC 3595A (soft), PC 3555D (average) and PC 3572D (hard). These three polyurethane types are distinguished with respect to their elasticity and strength. The shape-recovery behavior of these three types is depicted in FIG. 2.

This direct comparison clearly shows that the shape-recovery curves of the softer types of specimens clearly have other shape-recovery temperature ranges. The soft variants of the samples can detect hardly any maximum in shape recovery. With these samples, the shape recovery of the introduced orientations is superimposed by pure elastic shape recovery. For the planned use as a plastic stent, the hard polyurethane type PC-3572D is thus best suited, since it has the most clearly pronounced shape recovery. In addition, because of its high strength, the hard material also allows very small wall thicknesses with high stability, which in addition corresponds to the use of this type.

EXAMPLE 2

Production of Plastic Parts by Means of Extrusion

The extrusion of the carbothanes was carried out in an extruder based on the following angular data:

TABLE 2

Extrusion Parameters of Carbothanes

| Product | Zone 1 [° C.] | Zone 2 [° C.] | Zone 3 [° C.] | Zone 4 [° C.] | Melt [° C.] | Nozzle [° C.] | Pressure [N/mm²] |
|---|---|---|---|---|---|---|---|
| PC-3572D | 200 | 205 | 215 | 225 | 220 | 220 | 13.5–27 |

The extrusion was carried out as described above. The outside diameter of the specimen was 4 mm with a wall thickness of 0.5 mm.

EXAMPLE 3

Production of Plastic Parts by Injection Molding

The injection molding was preformed based on the following temperature profile:

| Product | Feed Temperature [° C.] | Mass Temperature [° C.] | Nozzle Temperature [° C.] |
|---|---|---|---|
| PC3572D | 190 | 200 | 205 |

The injection molding was carried out as described above. The dimensions of the specimens corresponded to those of the extrusion, whereby a demolding tilt of 1–2% was provided for the core.

EXAMPLE 4

Production of Plastic Parts by Immersion

A 5% carbothane solution in tetrahydrofuran was produced. An immersion rod with an outside diameter of 3 mm was immersed in the solution for 15 seconds. The wetted rod was raised from the solution and dried while being rotated in a flow of heat for 30 minutes. The immersion process was repeated several times until the desired wall thickness was reached. The finished polymer part was removed by the metal rod.

The immersion process can be performed in principle also with other solvents, such as, e.g., chloroform.

EXAMPLE 5

Stretching, Setting and Measuring the Shape Recovery

As actual stent production, reference can be made to introducing the shape memory, thus stretching with subsequent setting. In this process step, the actual product in its application diameter is from the blank. In addition, the desired activation temperature is determined in this process step by determining the stretching parameters.

In this respect, the prepared sample was clamped in the clamping device in such a way that it had a length of 50 mm between the clamping points. The sample was heated to 40° C. with the aid of the tempering cycle. This temperature was maintained for 10 minutes, so that the sample was thoroughly heated. The sample was expanded to 200%. The motor operated at a speed of 20 min-1 (this corresponds at a screw pitch of the spindle of 2.5 mm to a stretching of 50 mm/min). After one minute, the sample was expanded to 100 mm between the clamping points, and the motor was turned off.

Then, the specimen took up its internal stresses as much as possible through the relaxation of the plastic. During this so-called setting, the temperature was kept constant, since this setting temperature corresponds to the later activation temperature. After 15 minutes, the tempered liquid was drained off and replaced by cooled liquid. This temperature was maintained for several minutes, so that the specimen could cool thoroughly. The residual stress that is present in the cooled state in the sample was now also taken up when the slide was quickly brought in. With the applied temperature, the state of the sample was stable.
Study of the Shape Memory (Shape Recovery)

For the study of the shape recovery, the sample was slowly heated. A heating rate of 1° C./minute was selected. Starting from a specific temperature, shape recovery of the sample began. In this case, the measured-value recording system continuously plotted the temperature and the path covered. Within a certain temperature range, maximum shape recovery was expected. Shape recovery ended when the sample again reached almost its initial length of 50 mm. The recorded raw data were now available for further evaluation.

Parameters of the Execution of the Test:

TABLE 3

Standard Parameters

| Parameter | Value | Explanation |
| --- | --- | --- |
| Stretching temperature | 40° C. | This temperature must be at least as high as the setting temperature. |
| Stretching speed | 50 mm/min | At this speed, the molecules are stretched uniformly, and the heat that is produced in this case can be dissipated. |
| Degree of stretching | 100–400% | Depending on the elongation at tear of the material, various degrees of stretching are possible. |
| Setting temperature | 40° C. | At this temperature, the shape-recovery maximum is expected. |
| Setting time | 15 min | At this time, the material has taken up almost all internal stresses if a constant temperature is reached. |
| Freezing temperature | min. 20° C./min | A quick cooling can be targeted. |
| Freezing rate | −10° C. | At this temperature, the deformations are "frozen." |
| Heating rate | 1° C./min | To be able to record the shape recovery specifically by the temperature, a slow, uniform heating is necessary. |

EXAMPLE 6

Active-Ingredient-Loaded Plastic Parts a) Production by Extrusion

2% Dexamethasone was admixed in the granulate of PC 3572D. The extrusion was carried out with the parameters described in Example 2. Stents with the active ingredients prednisolone and triamcinolone acetonide were analogously produced at concentrations of 0.5 to 10% of the active ingredient.

b) Production by Injection Molding

2% Dexamethasone was admixed in the granulate of PC 3572D. The injection-molding process was carried out with the parameters described in Example 3. Stents with the active ingredients prednisolone and triamcinolone acetonide were produced analogously at concentrations of 0.5 to 10% of the active ingredient.

c) Production by Immersion

The production was carried out as in Example 4, but with an admixture of 2% dexamethasone in the polymer solution. Stents were analogously produced with the active ingredients prednisolone, acetylsalicylic acid, iloprost and triamcinolone acetonide at concentrations of 0.5 to 10% of the active ingredient.

d) Production by Immersion in Solutions with Varying Active Ingredient Concentration The production was carried out as in Example 4, but with admixtures of dexamethasone in concentrations of 0.5 to 10% in the different layers, such that the specimen had the highest concentration on the inside and the lowest active ingredient concentration on the outside.

e) Production by Immersion in Solutions with Different Active Ingredient Additions The production was carried out as in Example 4, but with admixtures of 2% dexamethasone in the solution, from which the inside layers were immersed, and 2% iloprost, from which the outside layers were immersed. Between the layers with varying active ingredient concentration, a separating layer that consists of active ingredient-free polyurethane was immersed.

f) Release Studies

Figure 3:
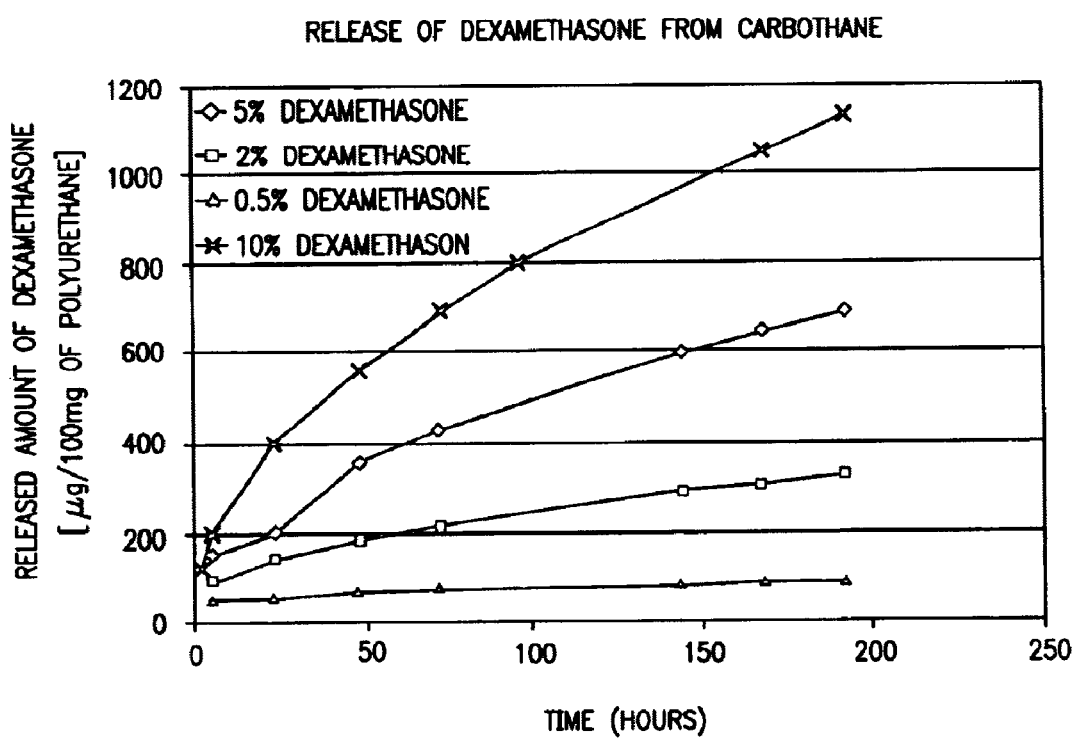

The release of the dexamethasone in the stents produced according to Example 6c) was determined in vitro over a period of 7 days. A continuous release of the active ingredient over the observation period was found (see FIG. 3).

The release studies with the stents loaded with the other medicinal active ingredients followed a similar course.

g) Stretching and Setting of the Active-Ingredient-Loaded Plastic Parts

The stretching and setting of the plastic parts loaded with active ingredients (stents) was carried out analogously to the process that is described above in Example 5. A shape memory was impressed on the stents by this treatment.

h) Production of Plastic Parts with the Addition of Contrast Medium

In the injection-molding process, test rods were produced with a proportion of 10% barium sulfate and compared to test rods without the addition of contrast medium. It was shown that the addition of barium sulfate makes the material more rigid: the yield stress increased by about 20%, the tensile strain increased by about 20%, and the modulus of elasticity increased by about 100%. The changes in the mechanical properties had only a relatively slight effect on the shape-recovery behavior: within the first 5 minutes of the shape recovery, no significant change in the shape recovery could be observed, accordingly the shape recovery was completed a little more slowly. The shape recovery of the specimen loaded with contrast media reached about 89% of the shape recovery of the contrast medium-free specimen.

What is claimed is:

1. A stent consisting essentially of a thermoplastic polyurethane with Shore hardness of 73A to 80D, which has a shape memory and a shape-recovery temperature of 35° C. to 50° C. and contains at least one active ingredient.

2. A stent according to claim 1, wherein only the inside surface and/or the outside surface of the vascular implant contains an active ingredient.

3. A stent according to claim 1, wherein the active ingredient concentration varies via the cross-section of the implant.

4. A stent according to claim 1, wherein the vascular implant contains two or more different active ingredients.

5. A stent according to claim 1, wherein the active ingredient is an x-ray contrast medium.

6. A stent according to claim 5, wherein the x-ray contrast medium is barium sulfate.

7. A stent according to claim 1, wherein the active ingredient is present up to a proportion or 30% by weight at a ratio to the polymer.

8. A stent according claim 1, wherein the active ingredient is released continuously after the implantation.

9. A process for preparing a stent according to claim 1, comprising processing a thermoplastic polyurethane together with an active ingredient into a blank in an injection-molding process at 160 to 240° C., and impressing a shape memory on the blank by stretching and setting.

10. A process for preparing a stent according to claim 1, comprising extruding a thermoplastic polyurethane together with an active ingredient at temperatures of 200 to 260° C. in a blank, and impressing a shape memory on the blank by stretching and setting.

11. A process for preparing a stent according to claim 1, comprising dissolving a thermoplastic polyurethane together with an active ingredient in a solvent to form a solution, immersing or pouring the solution to form a blank, and impressing a shape memory on the blank by stretching and setting.

12. A stent according to claim 1, wherein the thermoplastic polyurethane is polymer PC-3572D.

13. A stent according to claim 1, wherein the thermoplastic polyurethane has a Shore hardness of 71D.

14. A stent according to claim 1, wherein the active ingredient has an antiproliferative action on endothelium and/or smooth muscle cells or prevents an overflowing neointima from starting to form by keeping a thrombus from attaching to vascular wall.

15. A stent according to claim 1, wherein the active ingredient is selected from the group consisting of angiostatin, endostatin, iloprost, prostacyclin, endoxan, methotrexate, heparin, hirudin, clopidogrel, paclitaxel, doxazosin, thalidomide, rapamycin, trapidil, acetylsalicylic acid, dexamethasone, prednisolone, triamcinolone acetonide and epothilone.

16. A method for prophylaxis of restenosis comprising inserting a stent according to claim 1 into a patient in need thereof.

17. A stent consisting of a thermoplastic polyurethane with a Shore hardness of 73A to 80D, which has a shape memory and a shape-recovery temperature of 35° C. to 50° C. and contains at least one active ingredient.

18. A stent according to claim 1 wherein the stent is not made of wire which is coated with the thermoplastic polyurethane.

* * * * *

UNITED STATES PATENT AND TRADEMARK OFFICE
CERTIFICATE OF CORRECTION

PATENT NO. : 7,087,078 B2  Page 1 of 1
APPLICATION NO. : 10/432156
DATED : August 8, 2006
INVENTOR(S) : Gesine Hildebrand et al.

It is certified that error appears in the above-identified patent and that said Letters Patent is hereby corrected as shown below:

Column 10, line 41, reads "with Shore" should read -- with a Shore --
Column 10, line 57, reads "proporiton or 30%" should read -- proportion of 30% --

Signed and Sealed this

Sixth Day of March, 2007

JON W. DUDAS
*Director of the United States Patent and Trademark Office*